US008532736B1

(12) United States Patent
Malzbender et al.

(10) Patent No.: US 8,532,736 B1
(45) Date of Patent: Sep. 10, 2013

(54) APPARATUS AND A METHOD FOR QUANTIFYING PROPERTIES OF SKIN

(75) Inventors: Thomas Malzbender, Palo Alto, CA (US); Daniel G. Gelb, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1986 days.

(21) Appl. No.: 11/192,859

(22) Filed: Jul. 29, 2005

(51) Int. Cl.
*A61B 5/05* (2006.01)

(52) U.S. Cl.
USPC ............ 600/407; 600/473; 600/476; 382/128

(58) Field of Classification Search
None
See application file for complete search history.

(56) References Cited

U.S. PATENT DOCUMENTS

| | | | | |
|---|---|---|---|---|
| 5,016,173 A | * | 5/1991 | Kenet et al. | 382/128 |
| 5,456,260 A | * | 10/1995 | Kollias et al. | 600/477 |
| 6,008,889 A | * | 12/1999 | Zeng et al. | 356/73 |
| 6,021,344 A | * | 2/2000 | Lui et al. | 600/476 |
| 6,069,689 A | * | 5/2000 | Zeng et al. | 356/73 |
| 6,081,612 A | * | 6/2000 | Gutkowicz-Krusin et al. | 382/128 |
| 6,603,552 B1 | * | 8/2003 | Cline et al. | 356/417 |
| 2002/0087085 A1 | * | 7/2002 | Dauga | 600/476 |

OTHER PUBLICATIONS

Murhy et al, "Bidirectional Imaging and Modeling of Skin Texture" Oct. 17, 2003, France.*

* cited by examiner

*Primary Examiner* — Tse Chen
*Assistant Examiner* — Joel F Brutus

(57) ABSTRACT

Embodiments of the present invention pertain to methods and apparatuses for quantifying properties of skin. In one embodiment, data that describes a set of images of skin is received. A plurality of the images comprising the set of images were taken under a different lighting condition. Surface normals are computed based on the data and the computed surface normals are utilized to enable quantifying a property of the skin for the purpose of evaluating the skin.

22 Claims, 8 Drawing Sheets

APPARATUS AND A METHOD FOR QUANTIFYING PROPERTIES OF SKIN

TECHNICAL FIELD

Embodiments of the present invention relate to the field of skin evaluation. More specifically, embodiments of the present invention relate to quantifying properties of skin.

BACKGROUND

Presently, certain methods for evaluating the condition of skin are as much an art as a science. For example, dermatologists routinely perform preliminary diagnostics based on subjective feel and visual assessments. In other words, when trying to determine whether a skin region is cancerous, doctors frequently perform a preliminary evaluation based on the color of regions of skin and/or the roughness of a region of skin.

In most cases, preliminary evaluations are performed by looking at and feeling the skin and then performing a comparison between the actual skin condition and written or visual descriptions found in a book. In other cases, there may also be a reliance on previously evaluated skin conditions. That is, there is presently no simple way to characterize skin roughness or texture. Therefore, each evaluation is subject to a doctor's experience (e.g., time in the field, number of similar cases evaluated), visual acuity, sense of touch, and the like. Because of the subjective nature of the preliminary evaluation, an experienced doctor is more capable of performing a correct preliminary evaluation and a less experienced doctor would require more testing or expensive procedures, e.g., taking a sample, to arrive at the same result.

Therefore, it would be useful to the medical community to have objective quantifiable measurements of skin properties in order to evaluate skin more accurately as well as to provide quantifiable measurements that doctors can use to facilitate discussions between doctors. This information would also be valuable to the field of cosmetic evaluation.

For these and other reasons, a method and/or an apparatus that enables quantifying skin properties would be valuable.

DISCLOSURE OF THE INVENTION

Embodiments of the present invention pertain to methods and apparatuses for quantifying properties of skin. In one embodiment, data that describes a set of images of skin is received. A plurality of the images comprising the set of images were taken under a different lighting condition. Surface normals are computed based on the data and the computed surface normals are utilized to enable quantifying a property of the skin for the purpose of evaluating the skin.

BRIEF DESCRIPTION OF THE DRAWINGS

The accompanying drawings, which are incorporated in and form a part of this specification, illustrate embodiments of the invention and, together with the description, serve to explain the principles of the invention.

Figure 1:
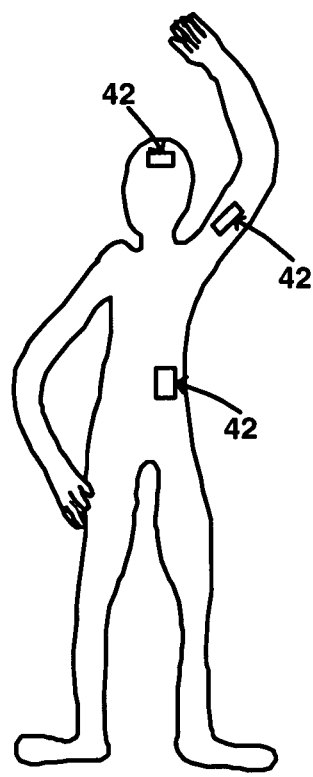
FIG. 1 depicts a person and a region of skin thereon according to one embodiment.

The drawings referred to in this description should not be understood as being drawn to scale except if specifically noted.

BEST MODE FOR CARRYING OUT THE INVENTION

Reference will now be made in detail to various embodiments of the invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following description of the present invention, numerous specific details are set forth in order to provide a thorough understanding of the present invention. In other instances, well-known methods, procedures, components, and circuits have not been described in detail as not to unnecessarily obscure aspects of the present invention.

Overview

Currently, the diagnosis of skin cancer is largely based on the appearance of a region of skin. Dermatologists learn to recognize the warning signs of cancer, among other things, based on the coloration, surface roughness, etc., of the region of skin to determine whether the region is cancerous or prone to becoming cancerous. This determination is largely subjective in nature. To train dermatologists, textbooks show photographic examples of suspect regions of skin.

Although the surface roughness of skin is used as a part of diagnosing skin cancer, quantifying the surface roughness of skin has been difficult if not impossible to date. An experienced dermatologist will feel the surface of the skin in attempting to determine whether the region is cancerous, prone to cancer, etc. However, feeling the skin is very subjective in nature. In one embodiment, the present invention enables a dermatologist to quantify properties of a region of skin to determine whether the skin is cancerous, prone to cancer, among other things. Also, as will be described herein, further embodiments of the present invention can be used for other types of skin evaluation, such as, for example, cosmetic evaluation.

According to embodiments of the present invention, a method and an apparatus for quantifying properties of skin for the purpose of evaluation is provided. In one embodiment, the method and apparatus can be employed in a clinical setting. In addition, embodiments are capable of being employed on any portion of skin on a body. Furthermore, there is no need to utilize polarized light or measure range data or derive three-dimensional surfaces. That is, the method and apparatus are well suited for utilization in two-dimensional space and therefore can be, in one embodiment, utilized without requiring any type of surface range data necessary to generate a three-dimensional image. Although, embodiments do not need to measure range data or derive three-dimensional surfaces, it is well within the scope of the claims to provide three-dimensional surface imagery.

Operation

With reference now to FIG. 1, a person is shown having a plurality of evaluatable regions of skin 42. Although a plurality of regions 42 are shown on the person, it is understood that there may be only a single region 42 being evaluated or a region 42 being evaluated in a location not shown such as the nose, back, and/or any other location on the human body. In addition, the region may be smaller or larger than that shown in FIG. 1. Furthermore, the region 42 may be any shape or configuration. The utilization of a rectangle as the shape of the region 42 herein is merely for purposes of brevity and clarity.

Figure 2A:
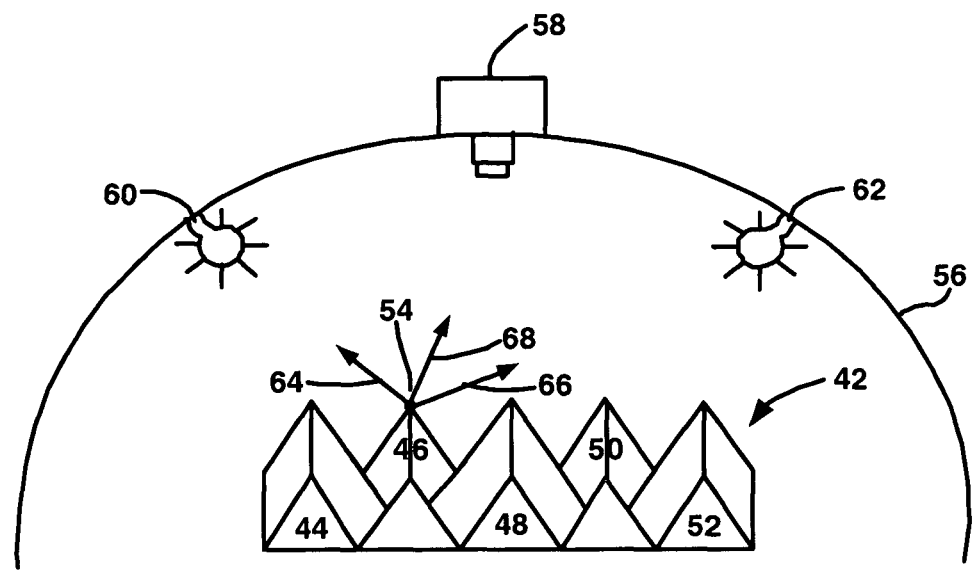
FIG. 2A depicts an apparatus that can be used for taking the set of images of the surface structure that is depicted in FIG. 1, according to another embodiment.

With reference now to FIG. 2A, in on embodiment, an imaging device 56 is used for acquiring a set of images of the region (or regions) of skin 42 under varying lighting conditions. More specifically, the pictures of the region of skin 42 are taken with the region of skin 42 illuminated from various respective directions. For example, a set of images of the region of skin 42 are obtained wherein a plurality of the images comprising the images in the set has been lighted from different direction. In one embodiment, imaging device 56 is a dome shaped device in which, a person or a region of skin is placed. In another embodiment, the imaging device 56 is placed over a person or a region of skin to perform the same task. In other words, the imaging device 56 is capable of being stationary or mobile and is equally functional in either setting. In one embodiment, a camera 58 such as, for example, a high-speed camera is placed on the top of the dome of the imaging device 56 pointing down through a hole. The camera 58 is then used to obtain a plurality of images of the region of skin 42 located within imaging device 56.

The imaging device 56 is used to position a camera 58 and a light source (e.g., 60 and/or 62) to take a set of pictures of the region of skin 42. In one embodiment, two light sources 60 and 62 are shown positioned at two example positions on the dome. A vector 64 represents a light source vector for the position 60 and a vector 66 represents a light source vector for the position 62. In another embodiment, a single light source is utilized and is moved through a plurality of locations around the imaging device 56.

In one embodiment, the camera 58 is fixed in position on the imaging device 56. In yet another embodiment, the camera 58 is mobile in its position with respect to the imaging device 56. In yet another embodiment, there is a plurality of cameras 58 in position on the imaging device 56. A vector 68 represents the eye point vector for the fixed position of the camera 58 is shown in accordance with one embodiment.

In operation, the camera 58 obtains an image of the region of skin 42 for each of a set of positions of the light source on the imaging device 56. Each position of the light source (e.g., 60 and 62) represents a different light source vector and the corresponding image obtained with the camera 58 yields a value for each texel of the region of skin 42. For example, images obtained from n different positions of the light source yields n values for each texel with each value corresponding to a different light source vector for the eye point vector 68. In one embodiment, the light source locations are predetermined. In another embodiment, the light source locations are not predetermined. For example, in one embodiment, the object can be photographed with a hand-held light source and then the light position can be figured out after the fact.

Sources of light, such as strobe boards, light emitting diodes (LEDs) and the like, are positioned (e.g., 60 and 62) around the dome for the purpose of illuminating the region of skin 42 from different lighting directions from the sources of light. The set of images are acquired by taking pictures, for example, at each of the different lighting directions. In one embodiment, light sources 60 and 62 are under a computer's control and are illuminated one at a time in rapid succession and a picture of the region of skin 42 is taken each time a source of light is illuminated. In another embodiment, a high-speed camera 58 is utilized in combination with controlling the sources of light 60 and 62 to capture the images. Although computer control of the lighting and high speed cameras are not a requirement for the operation of the imaging device 56, since it is difficult for people to be still for a long period of time, capturing the images quickly ensures quality imagery. Therefore, by utilizing the high speed camera and computer controlled illumination, the images can be acquired in an extremely short period of time, for example, 50 images in $1/10^{th}$ of a second.

Figure 2B:
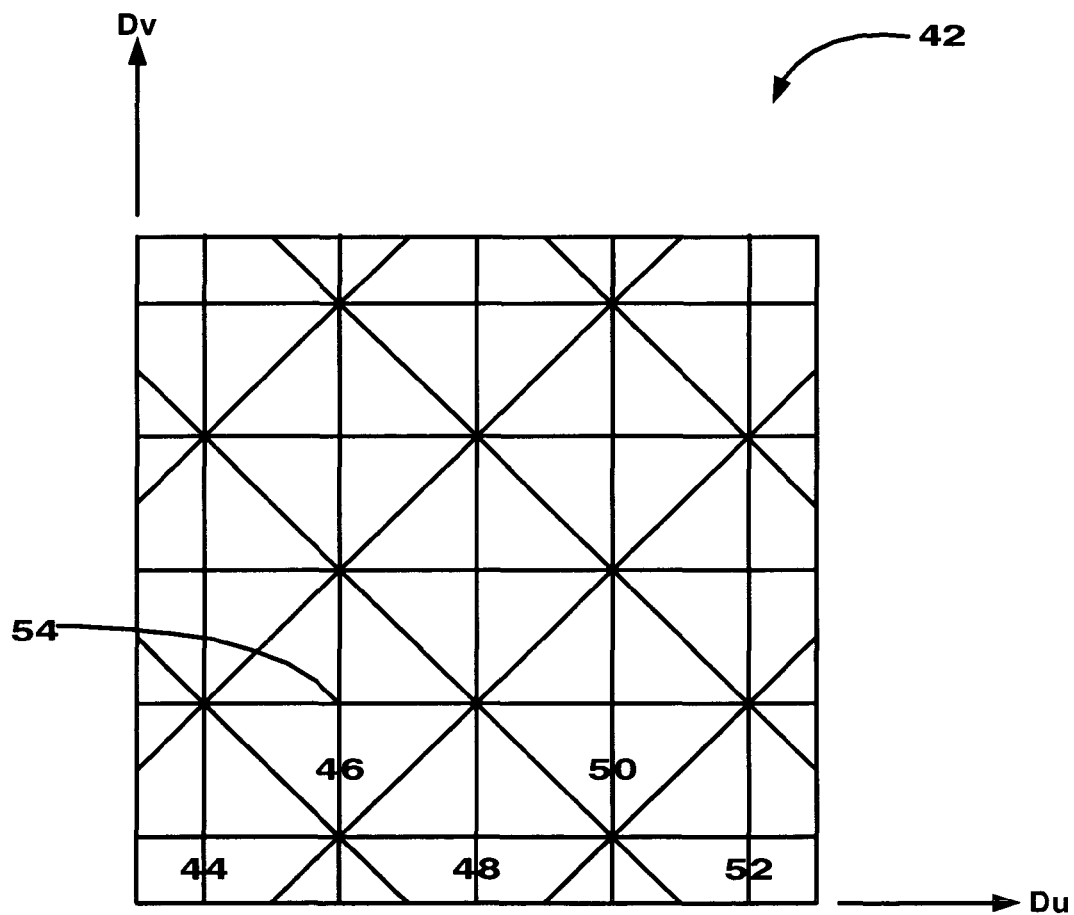
FIG. 2B depicts a top view a surface structure of the region of skin that a set of images can be taken of, according to one embodiment.

With reference now to FIG. 2B, a top view the region of skin 42 is shown. In one embodiment, the region of skin 42 is shown with the light vectors aligned to the imaginary axes $D_u$ and $D_v$. The alignment of the light vectors with the imaginary axis is not necessary, but is shown herein to simplify the mathematical equations for purposes of brevity and clarity. A sub area 54 represents one of the texels of the surface structure. The region of skin 42 is just one example of a surface structure of the region of skin 42 and it should be appreciated that any imaginable surface structure may be modeled, according to embodiments of the present invention. In general, the data describing the set of images that the imaging device 56 obtained is transmitted to the skin characterizer 200 of FIG. 3.

Figure 3:
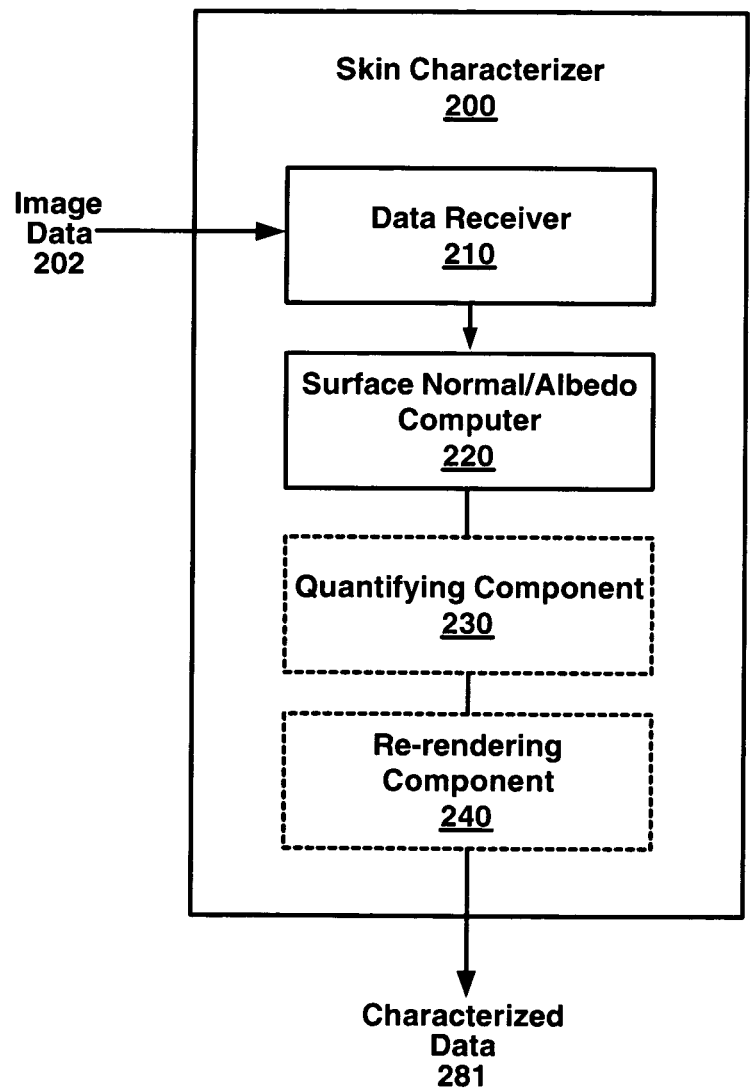
FIG. 3 depicts a block diagram of a skin characterizer for quantifying properties of skin for the purpose of evaluating skin, according to one embodiment.

With reference now to FIG. 3, a block diagram of a skin characterizer 200 for quantifying properties of skin for the purpose of evaluating skin is shown in conjunction with one embodiment. The skin characterizer 200 receives the data and uses the data to compute surface normals and/or albedos enabling quantification of properties, such as surface roughness and color, of the skin for the purpose of evaluating the skin. Further, the skin characterizer 200 is capable of displaying an image of the skin and varying image properties, such as specular reflectance (also commonly known as "shininess"), color and the like.

In one embodiment, the skin characterizer 200 includes a data receiver 210, a surface normal computer 220, an optional quantifying component 230, and an optional re-rendering component 240. The blocks that represent features in the skin characterizer 200 can be arranged differently than as illustrated, and can implement additional or fewer features than what are described herein. Further, the features represented by the blocks in the skin characterizer 200 can be combined in various ways.

The data receiver 210 receives the data that describes the set of images acquired from the region of skin 42. For example, the data describing the set of images that the imaging device 56 obtained is transmitted to the skin characterizer 200. The data receiver 210 receives the data. The surface normal computer 220 of the skin characterizer 200 uses the received data to calculate surface normals using one or more equations described in detail herein. The quantifying component 230 of skin characterizer 200 uses the surface normals to quantify properties of skin and a re-rendering component 240 of skin characterizer 200 uses the surface normals to vary the displayed properties of the image of the region of skin 42.

In one embodiment, the quantifying component 230 uses equations (described herein) for quantifying properties associated with skin, such as the color of the skin, the surface roughness of the skin, and the like. For example, one or more equations can be used to compute the color, the surface roughness, the topology of a region of the skin and the like. Further, the re-rendering component 240 uses equations to vary properties associated with skin, such as the color and/or the specular reflectance (e.g., shininess) that the skin is displayed with, and the like. For example, in one embodiment, the region of skin 42 is displayed with varying amounts of color and/or specular reflectance for purposes of easier evaluation and/or comparison.

In general, the equations described herein have parameters that are set to the values from the recovered data describing the set of images of the region of skin 42. Moreover, in one embodiment, the equations are used to quantify properties associated with skin by assigning values from the recovered data to the parameters of the equations. According to another embodiment, the equations are used to vary properties that an image of the skin is displayed with by varying the values assigned to the parameters of the equations. For example, the region of skin 42 can be made to look more specular (e.g., shiny) by varying the coefficient of specular highlight and the color of the subject's skin can be modified by varying the color value assigned to parameter(s).

In one embodiment, the quantifying component 230 of skin characterizer 200 uses the surface normals to quantify properties of skin. For example, the surface normal computer 220 uses equations, such as equation 1 and/or 2 (depicted below) to compute surface normals based on the data received by the data receiver 210. One version of a surface reflectance equation is represented by equation 1 below:

$$L(u,v;l_u,l_v)=a_0(u,v)l_u^2+a_1(u,v)l_u^2+a_2(u,v)l_ul_v+a_3(u,v)l_u+a_4(u,v)l_v+a_5(u,v) \quad (1)$$

where $l_u$ and $l_v$ represent two varying parameters or conditions.

For example, $l_u$ and $l_v$ can represent different orientations of light direction. The coefficients $a_0$ through $a_5$ are stored as well as the unscaled red, green, and blue colors per pixel.

In one embodiment, the set of images that are captured using the imaging device 56 are processed to recover an estimate of the geometric surface normal of each pixel. For each pixel, a low-order binomial model is fit to the collected brightness values using equation 1, among other things. Using equation 1 for each pixel (u, v) the luminance (brightness), L, of the pixel is a function of lighting direction (Lu, Lv). Coefficients ($a_0$-$a_5$) are computed and stored for each pixel to fit the measured luminance values using least mean squared, for example.

For a diffuse surface such as skin, the direction (Lu, Lv), that maximizes the luminance, L, is a good estimate for the geometric surface normal for that pixel. This is because a diffuse surface region will appear the brightest when illuminated perpendicular to its orientation, regardless of viewing direction.

The surface normal can be quickly recovered by setting $$\frac{\partial L}{\partial l_u} = \frac{\partial L}{\partial l_v} = 0.$$

Analytically solving equation 1 yields the following estimate for surface normal:

$$l_{u0} = \frac{a_2 a_4 - 2a_1 a_3}{4a_0 a_1 - a_2^2} \quad (2)$$
$$l_{v0} = \frac{a_2 a_3 - 2a_0 a_4}{4a_0 a_1 - a_2^2}$$

At this point, an estimate of the orientation of the surface for every pixel in the set of images has been recovered. This characterization (e.g., the orientation of the surface for every pixel) is independent of the surface color of the skin and is geometrical in nature, according to one embodiment.

According to one embodiment, the quantifying component 230 uses the surface normals to quantitatively measure the surface roughness of skin. A smooth area of skin will yield an "image" of surface normals that does not vary significantly. On the other hand, a rough area of skin will yield greater variation in the direction of the normals from pixel to pixel. The variance of the surface normals across these areas of skin can be used to quantify the surface roughness of the skin. For example, the quantifying component 230 can use a quantification such as (3) shown below. E.g., the sum of the variance of each component of the 3D normalized surface over a set of skin pixels:

$$\sigma_x^2 = \Sigma L_{ix}^2 - (\Sigma L_{ix})^2$$

$$\sigma_y^2 = \Sigma L_{iy}^2 - (\Sigma L_{iy})^2$$

$$\sigma_z^2 = \Sigma L_{iz}^2 - (\Sigma L_{iz})^2$$

$$\sigma^2 = \sigma_x^2 + \sigma_y^2 + \sigma_z^2 \quad (3)$$

Although the above discussion primarily refers to using luminance for quantifying the surface roughness of a person's skin, other methods can be used for quantifying skin properties, such as determining skin albedo. For example, the quantifying component 230 is used for quantifying the color of skin. In other words, it is well known that skin color is one of the distinguishing factors that differentiate malignant and benign skin growths. However, the color of a region of skin when it is photographed tends to be a function of the spectrum of the illuminant as well as the geometry of the region of skin. The variable lighting image methodology provided, for example, using the imaging device 56, has the capability of factoring out both of these variables (e.g., spectrum and geometry).

First, in one embodiment, the illumination color can be carefully controlled in the imaging device 56 when all the sources are identical flash bulbs. Second, the effect of surface geometry can be subtracted out, yielding a quantity that is referred to in the vision community as albedo. Generally, albedo is the true reflectance of a surface, (at arbitrary wave lengths—thus the true surface color) without regards to its lighting conditions. An estimate of surface albedo can be recovered simply by factoring out the lighting conditions used as described herein. Since this albedo is not dependent on imaging properties, albedo proves much more useful than a photograph of skin in determining whether a skin growth is malignant or benign. It shall be assumed herein that the term "color" includes albedo.

The re-rendering component 240 associated with the skin characterizer 200 enables the varying of image display properties, such as specular reflectance, color and the like. For example, the re-rendering component 240 can use the surface normals computed using equation 1, equation 2, or a combination of equations 1 and 2 to enable the surface of a displayed image of skin to be lit under new reflectance properties (e.g., specular reflectance). In another embodiment, an image of the surface of the skin can be displayed with very specular reflectance (e.g., very shiny) such that it is easier to see small geometric details on the skin's surface with these reflectance properties. More specifically, the standard Blinn/Phong lighting equation, as depicted below, can be used for varying the specular reflectance with which an image of region of skin 42 is displayed:

$$I = k_a l_a + k_d l_d (N \cdot L) + k_s l_s (N \cdot H)^n \quad (4)$$

With respect to equation (4), $k_a$, $k_d$, and $k_s$ are parameters that are varied to control the rendering of the skin surface. Basically, equation 4 states that the light intensity I for a particular pixel is a function of the sum of the ambient contribution $l_a$, the diffuse contribution $l_d$, and the specular contribution $l_s$, at that location.

According to another embodiment, the re-rendering component 240 varies a property, such as specular reflectance or color, when displaying an image of the region of skin 42 by varying a parameter associated with an equation, such as equation (4). For example, a GUI that includes sliding bars could enable a user to add or subtract out the amount of color or specular reflectance depicted in the displayed image of the region of skin 42. More specifically, as a user moves a sliding bar for specular reflectance, for example, the re-rendering component 240 would vary a corresponding parameter associated with equation (4). Similar processing could be performed for varying the amount of color with which an image of the region of skin 42 is displayed. Although the method is described manually herein, in another embodiment, the re-rendering component 240 will function automatically without user input.

Additionally, in one embodiment, the direction from which the image of the region of skin 42 is lit can also be varied. For example, since an imaging device 56 was used for capturing a set of images using varying lighting directions (or varying camera angles and therefore varying lighting conditions), the set of images being rendered are also variable. Therefore, the direction of lighting of the rendered image of the region of skin 42 is capable of being varied automatically or in response to a user moving their cursor around on the displayed image of the region of skin 42. For example, if the cursor is placed at the left of the displayed image of the region of skin 42, the lighting direction is displayed as if it were coming from the left of the displayed image of the region of skin 42. Similarly, if the cursor is placed to the right of the displayed image of skin, the lighting direction is displayed as if it were coming from the right of the displayed image of the region of skin 42.

Embodiments of the present invention are also useful for evaluating a person's skin remotely. In other words, an imaging device 56 is used to capture images and the associated data for the skin of a person in one part of the world. The images and the associated data could be transmitted to another location in another part of the world, where a skin characterizer 200 is used to enable the quantification of properties of skin for the purpose of evaluating skin as described herein.

For example, a doctor in a first location captures images of the region of skin 42 utilizing an imaging device 56 and sends the data to another doctor in a second location. The doctor in the second location will then use the skin characterizer 200 to quantify the properties of the region of skin 42. Similarly, the doctor at the second location would choose to display an image of the skin to enable performing an evaluation of the displayed skin. Therefore, a first doctor would be capable of receiving a second opinion or evaluation without requiring patient travel or imagery lighting concerns.

In another embodiment, the method is used as a part of cost cutting measures, for example, doctors in other parts of the world are frequently used for evaluating x-rays, and the like. By using one imaging device 56 in one location for capturing a set of images and another skin characterizer 200 in another location for quantifying characteristics of the skin or for displaying an image of the skin based on the captured images, embodiments of the present invention could be used, for example, in outsourcing diagnostics of skin to doctors located, for example, in Mexico or India.

In another embodiments of the present invention a 3D representation that is similar to the topology of a person's skin could be created. As a result, a dermatologist could actually feel and touch the created 3D representation of the person's skin as a part of determining whether the person has a malignant growth. For example, haptic rendering methods can be used to allow a physician to remotely feel a representation of the skin surface of a patient. Hence, the physician obtains the diagnostic benefit of feeling the patient's region of skin without requiring direct contact with the patient. Thus, embodiments in accordance with the present invention enable remote diagnosis.

Figure 4:
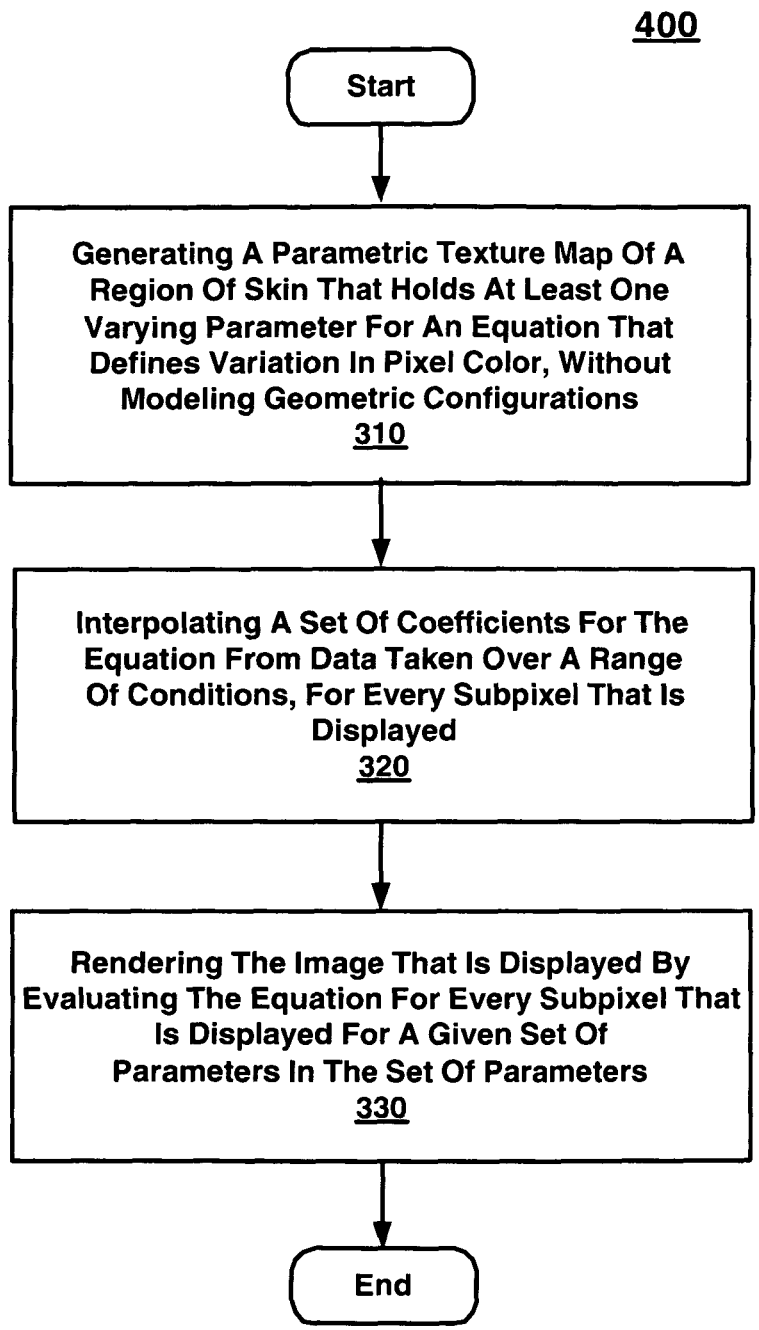
FIG. 4 is a flow chart illustrating a method for rendering an image that displays the aforementioned wide range of new effects, using a parametric texture map, in accordance with one embodiment of the present invention.

FIG. 4 is a flow chart 400 illustrating steps in a method for rendering an image that displays the aforementioned wide range of new effects, using a parametric texture map (PTM), in accordance with one embodiment of the present invention. The parametric texture map can be a polynomial according to one embodiment. As described herein, the PTM is in one embodiment used to derive the albedos. In another embodiment, the PTM is used to derive the surface normals. However, although PTM is the method described herein, it is one of a plurality of possible methods, such as photometric stereo, and the like which are also capable of deriving the surface normals and the albedos but which are not described in detail herein for purposes of brevity and clarity.

Although specific steps are disclosed in flowchart 400, such steps are exemplary. That is, embodiments of the present invention are well suited to performing various other steps or variations of the steps recited in flowchart 400. It is appreciated that the steps in flowchart 400 may be performed in an order different than presented, and that not all of the steps in flowchart 400 may be performed. All of, or a portion of, the embodiments described by flowchart 400 can be implemented using computer-readable and computer-executable instructions which reside, for example, in computer-usable media of a computer system or like device. As previously mentioned, a wide range of new effects can also be achieved through the use of a parametric texture map to represent any desired data.

In step 310, the present embodiment generates a parametric texture map of a subject that contains at least one varying parameter for an equation that defines variation in pixel color. The equation contains a set of varying parameters, each of the varying parameters corresponding to a varying condition. As such, the set of varying parameters is associated with a set of varying conditions. In accordance with embodiments of the present invention, the parametric texture map is generated without requiring any geometric modeling of a subject, as is utilized in a bump mapping technique of the prior art.

For purposes of this Application, the widely used term, "subject," is meant to expound on and not to disassociate itself from the previously used term, "object." In addition, for purposes of this Application, the widely used term, "condition," is meant to expound on and not to disassociate itself from the previously used term, "effect." Furthermore, although the term, "image," is used throughout this disclosure, the term is not limited to conventional film based photographs or to digital based photographs, but is directed towards all means of capturing images in one or more dimensions.

According to one embodiment, the parametric texture map represents any recovered data from the set of images taken of the region of skin 42. The recovered data reflects the set of varying conditions, such as the different lighting directions used while taking the set of images. In particular, each of the varying conditions in the set of varying conditions is sampled over a range within the desired dataset or sampled data. The data can reflect the pixel color value, among other things, for each of the color channels (e.g., red, green, or blue) displayed or represented over the range of conditions in the desired dataset.

Figure 5:
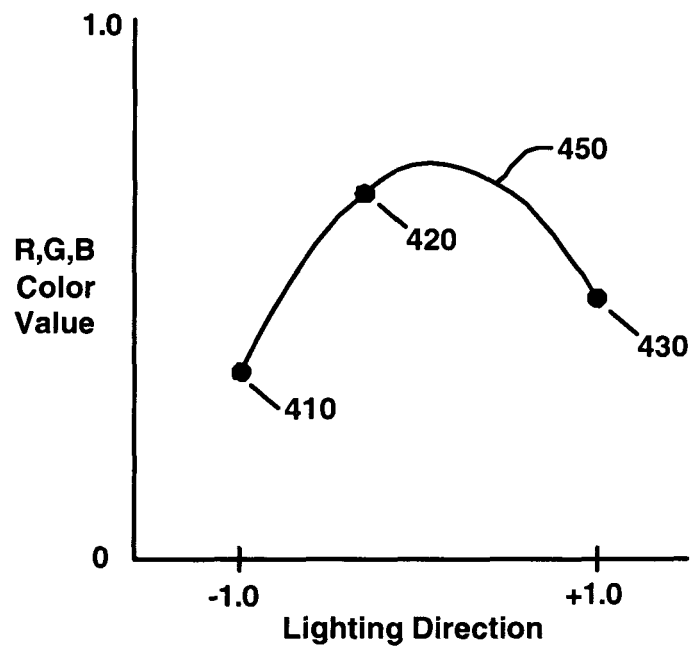
FIG. 5 is a graph which illustrates that the color channels have varying color values, in accordance with one embodiment of the present invention.

With reference now to FIG. 5, a diagram illustrating varying color values of color channels is shown in accordance with one embodiment of the present invention. On the vertical axis, the color value is represented as a value between zero and one, with zero representing the lightest color value, and one representing the deepest color value. The color values are representative of the RGB color values: red, green, and blue color values, respectively, in accordance with one embodiment of the present invention. For example, in the red color channel, a color value of one would give the deepest or fullest red available. A color value of zero would give the lightest red available.

The horizontal axis provides a range of values for the varying parameter, or varying condition. For purposes of illustration, diagram 500 shows a dataset varying in one dimension, or varying in one condition. Graph 450 represents color values for a corresponding color channel as a function of the condition varying in one dimension. Graph 450 shows a dataset of color values for one particular color channel with three data points: point 410, point 420, and point 430. These three points correspond to color values for a particular color channel under three separate conditions within the varying parameter.

Referring back to the flow chart 400, an embodiment of the present invention performs an interpolation of the dataset to obtain a set of coefficients for the equation, in step 320. A set of coefficients is determined for every color channel for every pixel that is displayed in creating the image. In each case, the equation is capable of generating or interpolating any color value for the color channel over the range of conditions taken within the dataset. Varying the direction of light that is used while acquiring images of the region of skin 42 is an example of varying conditions.

Diagram 500 provides an interpolation of the dataset of color values for a particular color channel that varies in one dimension. Alternatively, instead of representing color channels, diagram 500 can represent luminance (or brightness) values per pixel. The graph 450 between point 410 and point 430, the minimum and maximum conditions, respectively, provides an interpolation of the dataset of color values that is capable of generating a spectrum of color values over the full range of conditions in the dataset, for that particular color channel. A spectrum of images can be generated by combining color values for all the color channels of an image in the dataset.

In one embodiment, instead of storing color values for each subpixel to produce only one image, coefficients of an equation are stored. For example, in one embodiment, the equation is a polynomial equation and provides color values for a subpixel as a function of the varying condition or conditions (parameter or parameters, respectively). In another embodiment, the equation is a non-polynomial equation. The equations for each of the subpixels displayed create the parametric texture modeling of the image under the varying conditions or parameters.

Referring again to step 330, one embodiment renders the image by evaluating the equation for every color channel that is displayed. That is, the equation can be evaluated for every color channel since the coefficients for the equation were determined for every color channel in the previous step 320. The equation is evaluated for a given condition, or a given parameter in one dimension. For equations that vary in more than one dimension, the equation is evaluated for a particular condition in each dimension that varies, as represented by a given set of parameters in the set of varying parameters.

In one embodiment, instead of storing the color values for each color channel for every possible condition, the equation can be evaluated for each color channel under all the varying conditions. As such, when the particular condition, or set of conditions, is specified, a resulting color value for the color channel can be evaluated from the equation. The technique of representing each color channel with a red, green, and blue parametric texture map allows for modeling of the changes in the color of a color channel due to the changes in the conditions or parameters of the equation.

In one embodiment, the variation in the color of a color channel through the range of conditions is represented with a second order polynomial, as represented by equation 5 (displayed below), where $D_u$ and $D_v$ represent the two varying parameters or conditions.

In one embodiment, coefficients A1, A2, A3, A4, A5, and A6 are the parameters contained in the parametric texture map for evaluating the following second order polynomial equation:

$$Ci = A1D_u^2 + A2D_v^2 + A3D_uD_v + A4D_u + A5D_v + A6 \qquad (5)$$

where $D_u$ and $D_v$ are the 2D components of the user-defined vector commonly chosen to be the lighting direction.

The conditions, and the represented color values, in equation (4) vary in two dimensions, $D_u$ and $D_v$. The quadratic polynomial in equation (5) is fit to the dataset of color values associated with a particular color channel.

In one embodiment, equation (1) is a modification of equation (5) where $L_u$ and $L_v$ represent varying parameters or conditions. For example, $L_u$ and $L_v$ can represent different light source directions. The coefficients $a_0$ through $a_5$ are stored as well as the unscaled red, green, and blue colors per pixel.

In one embodiment, the coefficients are stored in a table, per color channel such as, Table 2 illustrated below. In general, table 2 illustrates the coefficients for equation (5) for a color channel contained within an exemplary pixel. The exemplary pixel has three-color channel that in combination form the entire spectrum of colors available to be displayed in the pixel, in one embodiment. The pixel is comprised of three-color channels: red, green, and blue.

TABLE 2

| RED | Green | Blue |
|---|---|---|
| A1 | A1 | A1 |
| A2 | A2 | A2 |
| A3 | A3 | A3 |
| A4 | A4 | A4 |
| A5 | A5 | A5 |
| A6 | A6 | A6 |

Table 2 of illustrates entries of coefficients for equation (5) for the color channel of the exemplary pixel. In the "RED" column, the various coefficients (A1-A6) of the second order polynomial function, representing the color values of the red subpixel across the defined set of conditions, are stored. In the "GREEN" column, the various coefficients (A1-A6) of the second order polynomial function, representing the color values of the green subpixel across the defined set of conditions, are stored. In the "BLUE" column; the various coefficients (A1-A6) of the second order polynomial function, representing the color values of the blue subpixel across the defined set of conditions, are stored.

In another embodiment, instead of solving for separate red, green, and blue PTM equations for each pixel that is displayed, the luminance over the entire color channels in each of the pixels is solved. In that case, since the luminance effect is relatively uniform over each of the color channels in a particular pixel, only one set of coefficients need be stored to solve the luminance for that particular pixel given a set of conditions. As such, a parametric texture map is used to reconstruct luminance for each pixel.

According to one embodiment, luminance redundancy is used to compute an unscaled color per pixel ($R_n(u,v)$, $G_n(u,v)$, $B_n(u,v)$)) that is modulated by a luminance model, $L(u,v)$ that is again dependent on the pixel, as follows:

$$R(u,v)=L(u,v)R_n(u,v);$$

$$G(u,v)=L(u,v)G_n(u,v); \text{ and}$$

$$B(u,v)=L(u,v)B_n(u,v). \quad (6)$$

As previously mentioned, in one embodiment, the user can choose to leave one of the parameters in the set of varying parameters constant for representing one-dimensional (1D) functions. For example, time variant functions can be represented in this manner, such as a photographic sequence of a scene as time varies during the day. Thus, the desired dataset would contain photographs throughout the day to reflect the variation of time on the subject. In another embodiment, the choice is automatic and no user input is needed.

Figure 6:
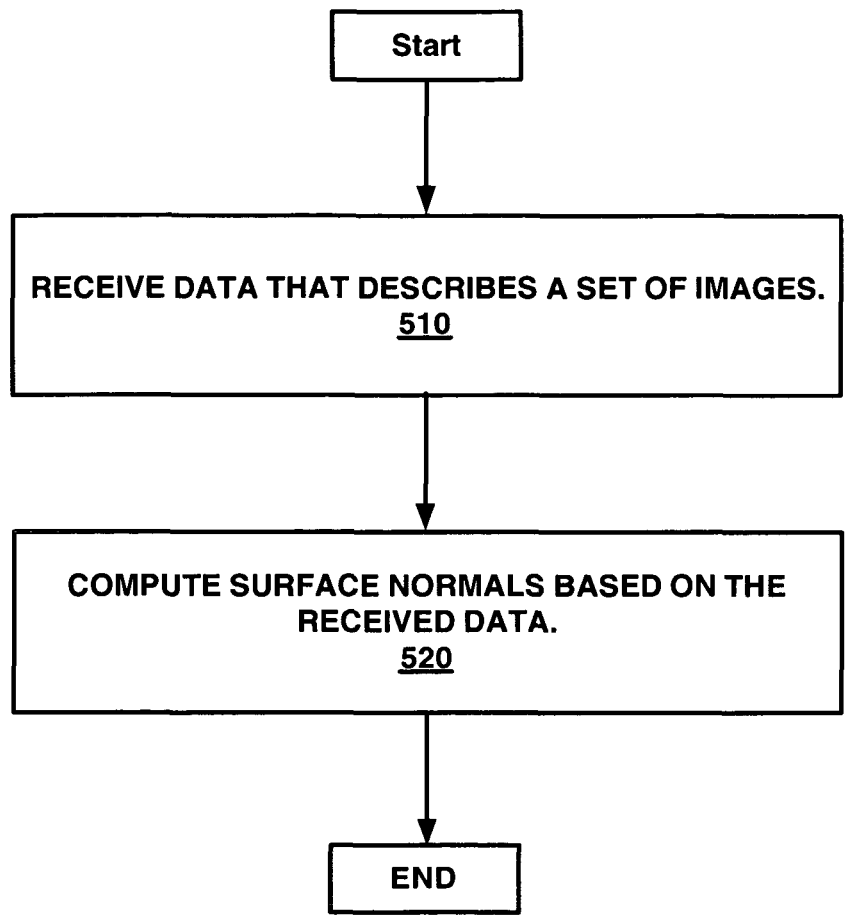
FIG. 6 is a flow chart illustrating a method for quantifying properties of skin, according to one embodiment of the present invention.

Referring now to FIG. 6, a flow chart 600 illustrating steps in a method for quantifying properties of skin for the purpose of evaluating skin is shown in accordance with one embodiment of the present invention. Although specific steps are disclosed in flowchart 600, such steps are exemplary. That is, embodiments of the present invention are well suited to performing various other steps or variations of the steps recited in flowchart 600. It is appreciated that the steps in flowchart 600 may be performed in an order different than presented, and that not all of the steps in flowchart 600 may be performed. All of, or a portion of, the embodiments described by flowchart 600 can be implemented using computer-readable and computer-executable instructions which reside, for example, in computer-usable media of a computer system or like device.

In preparation for step 510, the imaging device 56 of FIG. 2A is used to capture a set of images of the region of skin 42. As described herein, the images are captured under varying conditions, for example, by varying the direction of the light source that is used when taking images or other methods described herein. The set of images that are captured using the imaging device 56 are then processed to recover data that describes the set of images of the region of skin 42.

With reference now to step 510 of FIG. 6 and to FIG. 2, in one embodiment data that describes a set of images is received. For example, the data describing the set of images that the imaging device 56 obtained are transmitted to skin characterizer 200. In one embodiment, as described herein, the skin characterizer 200 receives the data and computes surface normals and/or albedos utilizing the methods described herein. In yet another embodiment, the skin characterizer 200 receives the data and computes surface normals and/or albedos utilizing comparable methods not described herein for purposes of brevity and clarity.

With reference now to step 520 of FIG. 6 and to FIG. 2, in one embodiment, surface normals and/or albedos are computed based on the received data. As described herein, the skin characterizer 200 receives the data in step 510 and uses the data to compute surface normals and/or albedos. In so doing, the skin characterizer 200 enables quantification of properties, such as surface roughness, color and the like, of the region of skin 42 for the purpose of evaluating the skin.

Figure 7:
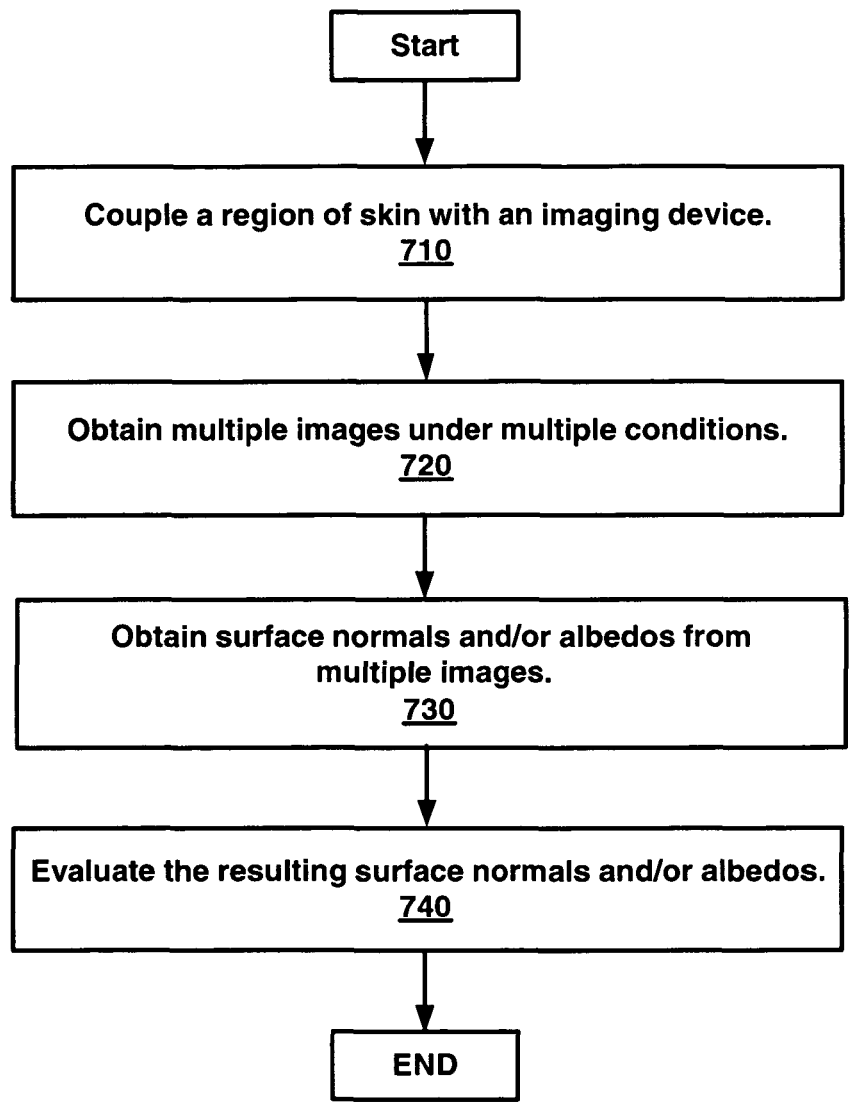
FIG. 7 is a flow chart illustrating a method for characterizing properties of skin for the purpose of evaluating skin, according to another embodiment of the present invention.

With reference now to FIG. 7, a flowchart 700 of the method for quantifying properties of skin for the purpose of evaluating skin is shown in accordance with one embodiment. In general, flowchart 700 is a summary of the method details described herein for purposes of brevity and clarity. It is appreciated that the steps in flowchart 700 may be performed in an order different than presented, and that not all of the steps in flowchart 700 may be performed. All of, or a portion of, the embodiments described by flowchart 700 can be implemented using computer-readable and computer-executable instructions which reside, for example, in computer-usable media of a computer system or like device. As previously mentioned, a wide range of new effects can also be achieved through the use of a parametric texture map to represent any desired data.

Referring now to step 710 of FIG. 7 and to FIG. 1, one embodiment couples a region of skin 42 (to be evaluated) with the imaging device (e.g., imaging device 56 of FIG. 2A). As described in detail herein, the region of skin 42 is in one embodiment inserted into the imaging device 56, and in another embodiment, the imaging device 56 is placed above the region of skin 42.

With reference now to step 720 of FIG. 7 and to FIG. 2A, one embodiment obtains multiple images under multiple lighting conditions. As described herein, the multiple images may be obtained from the imaging device 56 via a high-speed camera over a short period of time, or a regular speed camera over a longer period of time. As stated herein, the utilization of a high-speed camera allows a better opportunity to obtain a plurality of images without the subject moving the region of skin 42. In addition, as described herein, the multiple lighting conditions of the imaging device 56 are the result of a stationary camera and a single mobile light source, a plurality of mobile light sources or a plurality of fixed light sources. In another embodiment, the multiple lighting conditions are the result of a mobile camera and a single mobile light source, a plurality of mobile light sources or a plurality of fixed light sources.

Referring now to step 730 of FIG. 7 and to FIG. 3, one embodiment obtains surface normals and/or albedos from the multiple images. For example, as described herein, the imagery data from the imaging device 56 is provided to the skin characterizer 200 which evaluates the imagery data and applies the equations (or similar equations) described herein resulting in the surface normal and/or albedo results.

With reference now to step 740 of FIG. 7, one embodiment evaluates the resulting surface normals and/or albedos. As described herein, by reducing the analysis to scientific method instead of experience and subjective opinion, a standard and repeatable characterization of skin characteristics is achieved. In one embodiment, the resulting surface normals and/or albedos are automatically evaluated against a database to establish skin condition. In another embodiment, the resulting surface normals and/or albedos are displayed on a screen (or printout, or the like) for visual evaluation or comparison with other surface normal and/or albedo imagery. In yet another embodiment, the resulting surface normals and/or albedos are evaluated both automatically and manually.

Additionally, in one embodiment, a doctor or patient may want to track the skin properties over time and look for changes. That is, by utilizing a repeatable and quantitative characterization of the skin, the skin characterization process can be repeated at any interval over a period of time. That is, due to the quantification of the process, a new skin analysis can be compared with any or all of the previous skin evaluations. In addition, the light and/or time of each skin characterization can be varied (or remain the same) to provide a plurality of data sets related to a particular patient and particular portion (or portions) of skin thereon.

According to one embodiment, a scale can be used for quantifying a property of skin. For example, a scale from 1-10 could be used for quantifying the surface roughness of a person's skin or the amount of redness there is in a particular region of the person's skin. More specifically, a value of 1 may indicate that a person's skin is not rough whereas the value of 10 indicates that a person's skin is extremely rough or vice versa.

Therefore, embodiments provide a method and system for quantifying properties of skin. Furthermore, embodiments provide a method and system for quantifying properties of skin for the purpose of evaluating skin. In addition, embodiments provide repeatable and quantitative characterization of skin roughness. Moreover, embodiments provide repeatable and quantitative characterization of skin texture. In yet another embodiment, the quantitative characterization of the properties of skin can be used in medical, cosmetic, and other skin based applications.

While the invention has been illustrated and described by means of specific embodiments, it is to be understood that numerous changes and modifications may be made therein without departing from the spirit and scope of the invention as defined in the appended claims and equivalents thereof.

What is claimed is:

1. A method of quantifying properties of skin, the method comprising:
    receiving data that describes a set of images of skin, wherein a plurality of the images comprising the set of images were taken under a different lighting condition, the different lighting condition comprising a variance in a direction from which the plurality of the images is lit by one or more light sources; and
    computing surface normals based on the data, wherein said computer surface normals are utilized to enable quantifying a property of the skin for the purpose of evaluating the skin;
    displaying an image of the skin based on quantified properties of the skin, wherein a property with which the image of the skin is displayed is varied and selected from a group of properties consisting of specular reflectance and color.

2. The method as recited by claim 1, wherein the quantifying of the property of the skin further comprises:
    quantifying the property of the skin that is selected from a group consisting of color, surface roughness and albedo.

3. The method as recited by claim 1, wherein the evaluating of the skin is selected from a group consisting of:
    medical evaluation and cosmetic evaluation.

4. The method as recited by claim 1, further comprising:
    generating a haptic representation of the skin based on the received data.

5. The method as recited by claim 1, further comprising:
    capturing the set of images of the skin.

6. The method as recited by claim 5, wherein the receiving of the data that describes the set of images and the capturing the set of images are performed at different locations.

7. The method as recited by claim 1, further comprising:
    receiving data from at least a second set of images of said skin, said at least a second set of images taken at a second time; and
    comparing said at least a second set of images with a previous set of said images of said skin to provide a plurality of data sets related to a particular patient.

8. A skin characterizer for quantifying properties of skin for the purpose of evaluating skin, comprising:
    a data receiver for receiving data that describes a set of images of skin, wherein a plurality of the images comprising the set of images was taken under a different lighting condition, the different lighting condition comprising a variance in a direction from which the plurality of the images is lit by one or more light sources; and
    a surface normal computer for computing surface normals based on the data, wherein said computed surface normals are utilized to enable quantifying a property of the skin for the purpose of evaluating the skin;
    a re-rendering component for varying a property with which an image of the skin is displayed, and wherein the property with which the image of the skin is displayed is selected from a group consisting of specular reflectance and color.

9. The skin characterizer of claim 8, further comprising a quantifying component for quantifying the property of the skin that is selected form a group consisting of color, surface e roughness and albedo.

10. The skin characterizer of claim 8, wherein the evaluating the skin is selected from a group consisting of:
    medical evaluation and cosmetic evaluation.

11. The skin characterizer of claim 8, wherein the skin characterizer enables the generation of a haptic representation of the skin based on the surface normals.

12. The skin characterizer of claim 8, wherein the skin characterizer for quantifying properties of the skin is at a different location than an apparatus for capturing the set of images of the skin.

13. The skin characterizer of claim 8, wherein data is received from at least a second set of images of said skin, said at least a second set of images taken at a second time and compared with a previous set of said images of said skin to provide a plurality of data sets related to a particular patient.

14. A non-transitory computer-usable storage medium having computer-readable program code embodies therein for causing a computer system to perform a method of quantifying properties of skin, the method comprising:
    receiving data that describes a set of images of skin, wherein a plurality of the images comprising the set of images were taken under a different lighting condition, the different lighting condition comprising a variance in a direction from which the plurality of the images is lit by one or more light sources; and computing surface normals based on the data, wherein said computer surface normals are utilized to enable quantifying a property of the skin for the purpose of evaluating the skin;

displaying an image of the skin based on quantified properties of the skin, wherein a property with which the image of the skin is displayed is varied and selected from a group of properties consisting of specular reflectance and color.

15. The non-transitory computer-usable storage medium of claim 14, wherein the computer-readable program code embodied therein causes a computer system to perform the method, and wherein the quantifying of the property of the skin further comprises:

quantifying the property of the skin that is selected from a group consisting of color, surface roughness and albedo.

16. The non-transitory computer-usable storage medium of claim 14, wherein the computer-readable program code embodied therein causes a computer system to perform the method, and wherein the evaluating of the skin is selected from a group consisting of:

medical evaluation and cosmetic evaluation.

17. The non-transitory computer-usable storage medium of claim 14, wherein the computer-readable program code embodied therein causes a computer system to perform the method, and wherein the method further comprises:

receiving data from at least a second set of images of said skin, said at least a second set of images taken at a second time; and comparing said at least a second set of images with a previous set of said images of said skin to provide a plurality of data sets related to a particular patient.

18. A method of quantifying properties of skin, the method comprising:

receiving data that describes a set of images of skin, wherein a plurality of the images comprising the set of images were taken under a different lighting condition, the different lighting condition comprising a variance in a direction from which the plurality of the images is lit by one or more light sources; and computing albedos based on the data, wherein said computer albedos are utilized to enable quantifying a property of the albedo property for the purpose of evaluating the skin;

displaying an image of the skin based on quantified properties of the skin, wherein a property with which the image of the skin is displayed is varied and selected from a group of properties consisting of specular reflectance and color.

19. The method as recited by claim 18, wherein the quantifying of the property of the skin further comprises:

quantifying the property of the skin that is selected from a group consisting of color, surface roughness and albedo.

20. The method as recited by claim 18, wherein the evaluating of the skin is selected from a group consisting of:

medical evaluation and cosmetic evaluation.

21. The method as recited by claim 18, further comprising:

generating a haptic representation of the skin based on the received data.

22. The method as recited by claim 18, further comprising:

capturing the set of images of the skin.

* * * * *